(12) United States Patent
Doctors et al.

(10) Patent No.: US 8,082,923 B2
(45) Date of Patent: Dec. 27, 2011

(54) INTRA-ORAL DEVICE

(75) Inventors: Marc Doctors, Washington, DC (US); Randy Widen, Lusby, MD (US)

(73) Assignee: Randmark Dental Products, LLC, Lusby, MD (US)

( * ) Notice: Subject to any disclaimer, the term of this patent is extended or adjusted under 35 U.S.C. 154(b) by 205 days.

(21) Appl. No.: 12/379,194

(22) Filed: Feb. 13, 2009

(65) Prior Publication Data

US 2011/0100379 A1    May 5, 2011

Related U.S. Application Data

(60) Provisional application No. 61/064,048, filed on Feb. 13, 2008.

(51) Int. Cl.
*A61C 5/14* (2006.01)

(52) U.S. Cl. ............. 128/862; 128/859; 128/861; 433/6

(58) Field of Classification Search .................. 128/848, 128/859, 861, 862; 433/6
See application file for complete search history.

(56) References Cited

U.S. PATENT DOCUMENTS

| | | |
|---|---|---|
| 4,519,386 A | 5/1985 | Sullivan |
| 4,671,766 A | 6/1987 | Norton |
| 5,085,584 A | 2/1992 | Boyd |
| 5,277,203 A | 1/1994 | Hays |
| 5,513,656 A | 5/1996 | Boyd |
| 5,795,150 A | 8/1998 | Boyd |
| 6,516,805 B1 * | 2/2003 | Thornton ....................... 128/848 |
| 6,581,603 B1 | 6/2003 | Schames |
| 6,666,212 B2 | 12/2003 | Boyd |
| 7,234,467 B2 * | 6/2007 | Ball ............................... 128/848 |
| 2007/0023055 A1 * | 2/2007 | Roth .............................. 128/861 |
| 2008/0295850 A1 * | 12/2008 | Lesniak ........................ 128/862 |

\* cited by examiner

*Primary Examiner* — Patricia Bianco
*Assistant Examiner* — Keri J Nelson
(74) *Attorney, Agent, or Firm* — Ryndak & Suri LLP

(57) ABSTRACT

A device and method for relieving head, neck, facial, joint and tooth pain. An intra-oral, semi-custom, separating device, worn over the upper anterior teeth, allows at least one lower anterior tooth to contact the rear wall of the device within the user's freeway space and prevents lower posterior teeth from contacting upper posterior teeth. The device provides a method of deprogramming and releasing the muscles of the upper and lower jaws. The device comprises an extruded or molded shell made of a hard polycarbonate or similar hard plastic material. The internal surface of the shell is lined with a moldable thermoplastic resin with a low molding temperature which allows the user to mold the internal aspect of the device onto and over the teeth to produce a custom fitted device. This relieves the stresses, strains, pains and damage that can be caused by parafunctioning of the dental neuralmuscular system.

27 Claims, 2 Drawing Sheets

INTRA-ORAL DEVICE

RELATED U.S. APPLICATIONS

This application claims the benefit of U.S. provisional Application No. 61/064,048 filed Feb. 13, 2008 and entitled "Bite Device." The foregoing application is hereby incorporated herein by reference.

FIELD OF THE INVENTION

The present invention relates generally to intra-oral devices and, in particular, a mass produced, semi-custom, intra-oral separator device, intended to be worn by the user for the elimination or relief of grinding, clenching, bruxing, and related parafunctional habits, as well as head, neck and jaw related pain. Grinding, clenching and bruxing and related parafunctional habits can produce structural damage to, and disease of, the teeth, gums and supporting structures including the temporomandibular joint.

BACKGROUND OF THE INVENTION

There is an enduring need for an inexpensive and effective device and method for the relief of head, neck, facial, joint and tooth pain caused by the parafunctional movement of the jaws and teeth. The design and function of the present invention are different than the prior art in form, function, cost and potential for mass usage.

A variety of stressors affect the neuromuscular system of the head and neck. Among them are abnormal dental contacts, muscle tension and spasms, psychological stress factors, genetic predispositions, physical trauma and inflammation. In the presence of stressors the jaw muscles contract irregularly or parafunctionally causing the hitting together of the teeth. This interarch dental contact triggers headaches, both radiating and migraine, muscular tension, inflammation, structural damage to ligaments and tendons, fractures and excessive wear of the teeth, arthritic changes to the temporomandibular joint and periodontal disease. The pain generated radiates to other muscles, namely muscles of chewing and posture within the head, neck and back. The cycle of pain and structural damage thus created becomes the motivation for the efforts to design a device and method to minimize or eliminate these symptoms.

The prior art generally employs various platforms and protuberances to separate the teeth beyond the freeway space and beyond the physiologic rest position, making them less effective in eliminating pathologic muscle engrams and less likely to disrupt the cycle of pain and structural damage. The wider the mandible is forced to open by these platforms and protuberances, the more neuromuscular feedback is created and the less likely these devices are to disrupt the existing pathologic muscle engrams. In addition, these devices often require fittings by dental professionals and are therefore inconvenient and expensive for mass usage. By contrast, the device of the present invention is customizable by the user and, if available commercially at the retail level, would be relatively inexpensive. The device of the present invention functions within the freeway space to effectively deprogram the neuromuscular system of the head and neck by preventing contact of the upper and lower posterior teeth.

The prior art focused on the use of medications for pain relief or the fabrication of devices whose goal was to separate the teeth and reposition the jaws. Typical of these devices are U.S. Pat. No. 4,671,766 to Norton; U.S. Pat. No. 4,519,386 to Sullivan; U.S. Pat. No. 5,277,203 to Hays; U.S. Pat. No. 6,581,603 to Schames; and U.S. Pats. Nos. 5,085,584; 5,513,656; 5,795,150; and 6,666,212 to Boyd.

These treatments are often extremely expensive and/or ineffective. What is needed is a device that is readily and easily obtained at a reasonable cost and is simple to customize and use.

The present invention takes into account the need to eliminate the forced positioning of a person's mandible to or beyond the physiologic rest position. The freeway space, or interocclusal space, is defined as that distance between the physiologic rest position and the first point of contact of the upper and lower teeth when the jaws are brought together in closure. The freeway space has been observed to usually be between 2 and 7 millimeters (mm) with an approximate average for adults of 3.5 mm. The physiologic rest position is the position assumed by the mandible when the head is in an upright position, the neuromuscular system is in equilibrium in minimum tonic contraction and the condyles are at rest. The more an intra-oral device forces the mandible to open beyond the physiologic rest position, the more active neuromuscular feedback mechanisms become. This feedback triggers pathologic engrams. An engram is a memorized pattern of muscle activity. Pathologic engrams may also be eliminated by occlusal adjustment, reconstruction, retraining or through the use of medication. Thus the cycle of pain and structural damage can be interrupted temporarily or permanently. The prior art causes the mandible to be forced open beyond the limit of the freeway space, making it less likely to interrupt the cycle of pain and structural damage. What is needed, then, is a device that functions only within the freeway space while effecting disclusion of the posterior teeth and while maintaining clearance within the freeway space, thereby eliminating or significantly reducing pathologic engrams.

The prior art, directed to the reduction of headaches and temporomandibular joint (TMJ) pain, functions outside of a person's freeway space unless altered by a dental professional. Without this expensive and inconvenient adjustment, pathologic muscle engrams may remain, preventing the neuromuscular system from achieving the physiologic rest position. The current invention allows the user to fit the device to function only within the freeway space.

Posterior disclusion with an anterior bite device is simple and well understood. It is based on the concept that the temporomandibular joint will seat itself physiologically if the proprioceptive interferences of the teeth and periodontal ligaments are removed. Thus the neuromuscular system will function freely within the freeway space. Once a patient's pathologic muscle engrams have been eliminated, the temporomandibular joint becomes stable. In order to decrease the likelihood that the cycle of pain and structural damage returns, an occlusal adjustment with or without occlusal reconstruction may be necessary.

SUMMARY OF THE INVENTION

In one embodiment of the present invention, the external shell of the claimed device allows for the user to fit the device close to the incisal, lingual and labial surfaces of the upper anterior teeth, also referred to as upper incisors. Contact on the device by lower anterior teeth, also referred to as lower incisors, only within the freeway space, promotes more predictable release of muscle engrams than contact on a device outside the freeway space. In addition, this device does not require fittings by dental professionals and is designed for easy adaptation by a user. It is anticipated the device will be moderately priced and affordable by the great majority of those who need it.

One embodiment of the present invention relates to an intra-oral device comprising a body having a substantially angled front wall and a substantially angled rear wall, the front wall having an inner and outer surface and the rear wall having an inner and outer surface; wherein the front and the rear wall are positioned to receive the incisal edges of a user's upper incisors; wherein the outer surface of the rear wall is configured within the user's freeway space to contact at least one lower incisor at an area of contact only within the user's freeway space to prevent contact of the user's premolars and molars; wherein when the user's mandible is in the physiologic rest position there is no contact on the device by any of the user's lower teeth; wherein the inner surface of the front wall is configured to be placed adjacent to the facial surface of the user's upper incisors; and wherein the inner surface of the rear wall is configured to be placed adjacent to the lingual surface of the user's upper incisors.

One embodiment of the present invention relates to a method for preventing head, neck, facial, joint and tooth pain, the method comprising placing a device within a user's oral cavity, the device having an angled front wall and an angled rear wall, each wall with an inner and outer surface, wherein the angles of the front wall and the rear wall form an apex with moldable plastic resin disposed along the inner surfaces of the front and rear wall, the apex configured to receive the incisal edges of a user's upper incisors; positioning the device such that the front wall of the device is adjacent to the labial surface of the user's upper incisors and the inner surface of the rear wall is disposed adjacent to the lingual surface of the upper incisors; and configuring the device to contact at least one lower incisor within the user's freeway space to prevent contact of a user's premolars and molars.

One embodiment of the present invention relates to a method for manufacturing an intra-oral device, the method comprising forming a hard plastic resin shell having an angled front wall and an angled rear wall, each wall with an inner and outer surface, wherein the angles of the front wall and the rear wall form an apex with moldable thermoplastic resin disposed along the inner surfaces of the front and rear wall, the apex configured to receive the incisal edges of a user's upper incisors; configuring the front wall of the device to fit substantially flush against the labial surface of a user's upper incisors; configuring the inner surface of the rear wall to fit substantially flush against the lingual surface of a user's upper incisors; and adhering to the inner surfaces of the front and rear walls a moldable thermoplastic resin.

One embodiment of the present invention relates to an intra-oral product comprising a body having a substantially angled front wall and a substantially angled rear wall, the front wall having an inner and outer surface and the rear wall having an inner and outer surface; moldable thermoplastic resin material disposed along the inner surface of the front and rear walls; wherein the front and the rear wall are positioned to receive the incisal edges of a user's upper incisors; wherein the outer surface of the rear wall is configured to contact at least one lower incisor at an area of contact only within the user's freeway space to prevent contact of the user's premolars and molars when the user's mandible closes past the physiologic rest position; wherein the inner surface of the front wall is configured to be placed adjacent to the labial surface of the user's upper incisors; wherein the inner surface of the rear wall is configured to be placed adjacent to the lingual surface of the user's upper incisors; and wherein the moldable thermoplastic resin is capable of being molded by a user.

These and other objects and advantages of the invention will be apparent from the following description, the accompanying drawings and the appended claims.

BRIEF DESCRIPTION OF THE DRAWINGS

While the specification concludes with claims particularly pointing out and distinctly claiming the present invention, it is believed the same will be better understood from the following description taken in conjunction with the accompanying drawings, which illustrate, in a non-limiting fashion, the best mode presently contemplated for carrying out the present invention, and in which like reference numerals designate like parts throughout the Figures, wherein:

DETAILED DESCRIPTION OF THE INVENTION

Figure 1:
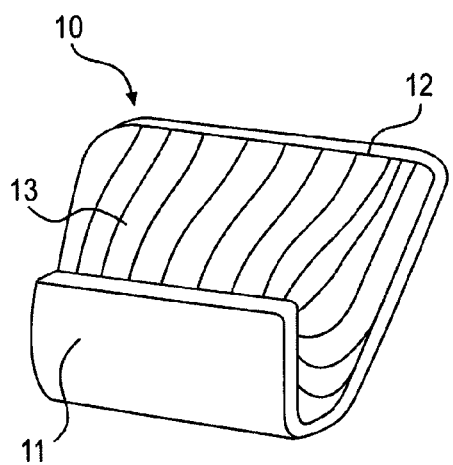
FIG. 1 shows a perspective view of an embodiment of the present invention as seen from an inferior-anterior-lateral view with thermoplastic installed inside hard shell.

The present disclosure will now be described more fully with reference to the Figures in which various embodiments of the present invention are shown. The subject matter of this disclosure may, however, be embodied in many different forms and should not be construed as being limited to the embodiments set forth herein.

Before explaining the features of this embodiment of the invention in detail, it should be understood that the invention is not limited in its application to the details of construction and arrangement of components set forth in the following description or illustrations in the drawings. The invention is capable of other embodiments and variations that will occur to those skilled in the art upon reading this disclosure. Also, it is to be understood that the phraseology and terminology used herein is for the purpose of description and should not be regarded as limiting.

Figure 2:
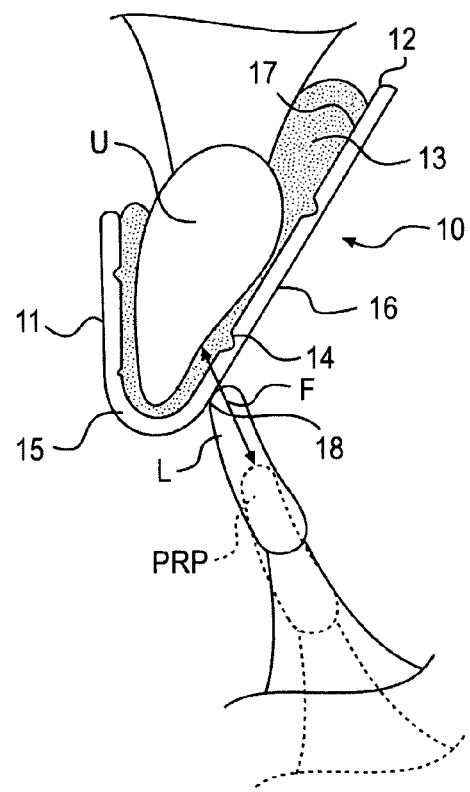
FIG. 2 shows a central section of the embodiment of the present invention of FIG. 1 with upper incisors in place in the device and lower incisors in contact within the user's freeway space on the outside rear surface of the device.
Figure 2A:
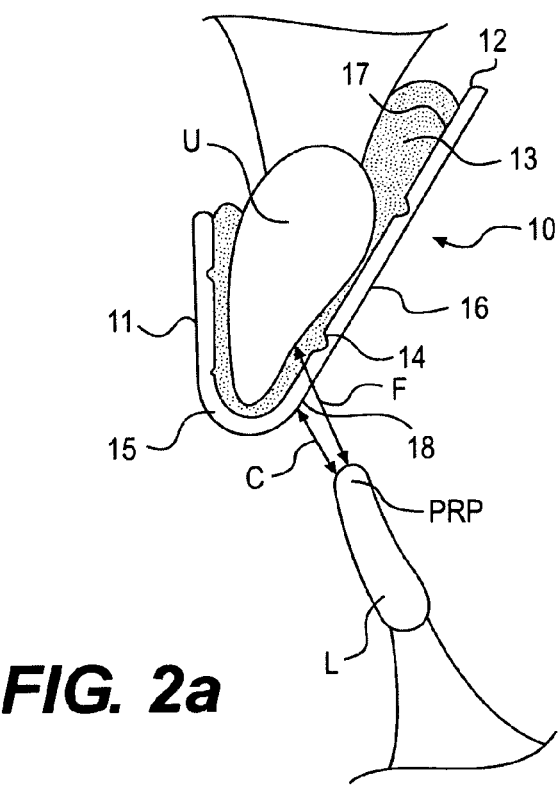
FIG. 2a shows a central section of the embodiment of the present invention of FIG. 1 with upper incisors in place in the device and the lower teeth in the physiologic rest position and not in contact with the device.

As illustrated in FIGS. 1-4, a semi-custom inter-occlusal separator device, constructed in accordance with one embodiment of the present invention, is comprised of a hard plastic main body 10 with thermoplastic disposed upon the inner surfaces of the main body 10 which is configured to be positioned on a user's teeth. In particular, the main body 10 is comprised of an angled front wall 11 and an angled rear wall 12. Front wall 11 approximates the angle and configuration of the labial surfaces of maxillary (also termed "upper" herein) incisors U and anterior maxillary dental arch and the rear wall 12 approximates the angle and configuration of the lingual surfaces of maxillary incisors U and anterior maxillary dental arch. In one or more embodiments, the front wall 11 is configured to fit substantially flush against the labial surface of a user's upper incisors U. In one or more embodiments, the rear wall 12 is configured to fit substantially flush against the lingual surface of a user's upper incisors U and to contact the user's lower incisors L only within the user's freeway space F, as illustrated for example in FIG. 2, with freeway space F being indicated by the double arrow extending from upper incisor U through area of contact 18 to the position of a lower incisor at the physiologic rest position PRP, depicted in phantom lines. As further illustrated in FIG. 2a, where lower incisor L is depicted in the physiologic rest position PRP, lower incisor L does not contact outer surface 16 or any other part of the device when the mandible is at physiologic rest, and thus, nor do any of the lower teeth. A clearance C is shown in FIG. 2a between lower incisor L and outer surface 16. While main body 10 is described above as being constructed of hard plastic, one skilled in the art recognizes that it may be constructed of any suitable material known or used in the art.

The angle of front wall 11 and the angle of rear wall 12 form an apex 15, approximating the angle of the labial and lingual surfaces of maxillary incisors U. Apex 15 is configured to receive a user's upper incisors U. As is apparent in FIG. 2 and FIG. 4, when the device is in place, the incisal edges of the lower incisors L contact outer surface 16 within freeway space F when the user's law closes, preventing the lower posterior teeth from coming into contact with the upper posterior teeth. The lower incisors L are in contact with the device as the mandible nears the end of its hinge arc of closure in one embodiment. The thickness between outer surface 16 and inner surface 17 is approximately 1.25 mm. The thickness of thermoplastic resin 13 is initially approximately 0.5 mm, before the device is custom molded and fit, but resin 13 is reduced to a negligible thickness by spreading and forming when resin 13 is at a molding temperature and a user pushes the device 10 against the user's upper incisors U to customize the device. Thus, the total approximate distance after the device is custom molded and fit between a user's upper and lower incisors L when the user's lower incisors L contact the device is approximately 1.25 mm, where the inner surface of the outer shell 16 becomes substantially flush against the lingual surface of the user's upper incisors U so that the device is disposed within the user's freeway space. While an embodiment of the present invention is described above with specificity, one skilled in the art recognizes that the thickness between the outer surface and inner surface, as well as the thickness of the thermoplastic resin may vary, although keeping these layers purposely thin is imperative to ensure that the device functions only within the freeway space, leaving a clearance C within the freeway space of a user, so that the lower teeth of the user do not contact the device such that the mandible is caused to open beyond the physiologic rest position when the device is worn in accordance with the invention. The thermoplastic resin 13 may be comprised of thermoplastic acetate co-polymer resin, such as [a] DuPont Elvax® resin or other material with similar properties, fixed in place on the inner surfaces of front wall 11 and rear wall 12 by detents 14, as shown in FIG. 2. The thermoplastic resin may also be retained and/or fastened on the inner surfaces of walls 12 and 14 by use of adhesive, mechanical restraints, or any other similar attachment means known in the art.

In the above-described embodiment, to customize the device, the device is placed in water at approximately 150° F. to soften the moldable thermoplastic resin. The device is then fitted and molded by the user. To fit and mold the device, the user pushes the softened moldable thermoplastic resin onto upper incisors U until the teeth "seat" to the apex of the interior angle between the front and rear walls 11, 12 of the device. The user then closes mandibular (also termed "lower" herein) incisors L against outer surface 16 of device 10 to adapt the device substantially flush against the lingual surfaces of the upper incisors U within the device.

Figure 4:
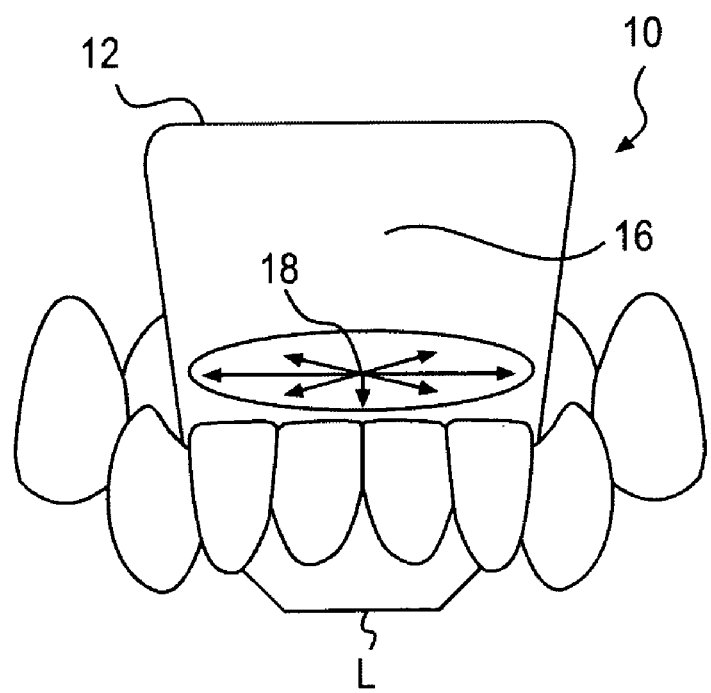
FIG. 4 shows a rear perspective view of the embodiment of the present invention of FIG. 1 in place on the upper incisors indicating the area of lower teeth contact within the user's freeway space on the outside rear surface of the device.

FIG. 2 and FIG. 4 show an embodiment of the present invention in place after molding and lower teeth in contact at area of contact 18, with outer surface 16 of the device, a position from which the user can move the mandibular anterior incisors laterally, protrusively and retrusively along the area of contact 18, on outer surface 16.

Figure 3:
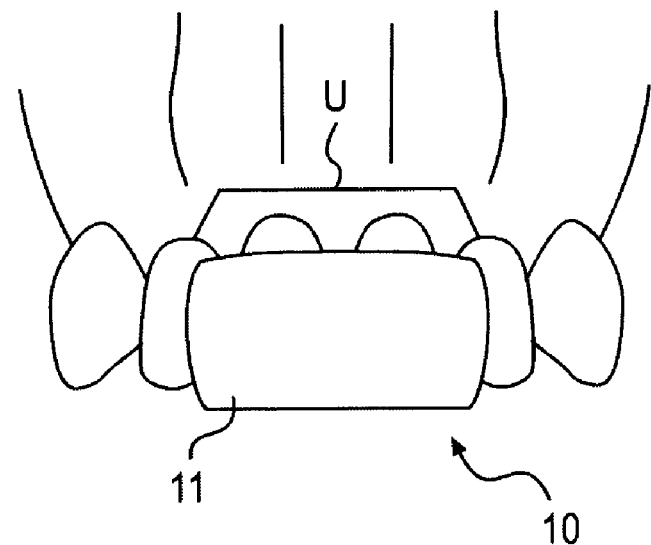
FIG. 3 shows an anterior perspective view of the embodiment of the present invention of FIG. 1 in place on the upper anterior teeth.

FIG. 3 shows a front view of the extent of coverage of an embodiment of the present invention in place on the upper anterior teeth.

FIG. 4 shows an area of contact 18 of mandibular incisors L, which allows mandibular incisors L to proprioceptively sense contact within the freeway space with outer surface 16 of an embodiment of the present invention, and to initiate release of parafunctional pathologic muscle engrams. More particularly, the reprogramming of muscle engrams can lead to the reduction of symptoms of parafunction from occlusal stress or psychological initiators. In one or more embodiments, by effecting the release of pathologic muscle engrams because the device functions only within the freeway space, the invention may proprioceptively, as opposed to forcibly, direct the user's mandible to the physiologic rest position. By "proprioceptively," it is meant that contact of lower incisors L with the device as the jaw is closing within the freeway space, and therefore already closed past the physiologic rest position, causes a natural relaxation response in which the jaw reflexively opens to the physiologic rest position, upon sensing contact.

The foregoing descriptions of specific embodiments of the present invention are presented for purposes of illustration and description. They are not intended to be exhaustive or to limit the invention to the precise forms disclosed. Obviously, many modifications and variations are possible in view of the above teachings. While the embodiments were chosen and described in order to best explain the principles of the invention and its practical applications, thereby enabling others skilled in the art to best utilize the invention, various embodiments with various modifications as are suited to the particular use are also possible. The scope of the invention is to be defined only by the claims appended hereto, and by their equivalents.

What is claimed is:

1. An intra-oral device custom fit for a user, comprising:
    a body having a substantially angled front wall and a substantially angled rear wall, the front wall having an inner and outer surface and the rear wall having an inner and outer surface;
    wherein the front and the rear wall are configured to receive the incisal edges of the user's upper incisors;
    wherein the outer surface of the rear wall is configured to be disposed within the user's freeway space and not in contact with the user's lower teeth when the user is in the physiologic rest position and to prevent contact of the user's upper and lower premolars and molars when the user's mandible closes past the physiologic rest position.

2. The device according to claim 1, wherein the rear wall of the device is configured to be located within the user's freeway space to contact at least one of the user's mandibular incisors at an area of contact only within the freeway space.

3. The device according to claim 1,
    wherein the inner surface of the front wall is configured to be placed adjacent to the labial surface of the user's upper incisors; and wherein the inner surface of the rear wall is configured to be placed adjacent to the lingual surface of the user's upper incisors.

4. The device according to claim 3, further comprising an amount of moldable thermoplastic resin material disposed along the inner surfaces of the front and rear walls.

5. The device according to claim 4, further comprising means to retain moldable material within the inner surfaces of the front and rear walls.

6. The device according to claim 5, wherein the means for retaining the moldable material comprise detents on the inner surfaces of the front and rear walls.

7. The device according to claim 5, wherein the means for retaining the moldable material comprise adhesive on the inner surfaces of the front and rear walls.

8. The device according to claim 4, wherein the thermoplastic resin material is capable of being molded at a temperature of approximately 150 degrees Fahrenheit.

9. The device according to claim 4, wherein the thermoplastic resin material is comprised of an ethylene vinyl acetate resin.

10. The device of claim 3,
wherein the inner surface of the front wall is configured to be placed substantially flush against the labial surface of the user's upper incisors; and
wherein the inner surface of the rear wall is configured to be placed substantially flush against the lingual surface of the user's upper incisors.

11. The device according to claim 1, wherein the device is configured to allow the user's mandibular incisors to move along the mandibular hinge arc of closure until at least one of the user's lower incisors contacts the device.

12. The device according to claim 1, wherein the device is configured to allow the user's mandibular incisors to move laterally, retrusively and protrusively along the area of contact.

13. A method for preventing head, neck, facial, joint and tooth pain, the method comprising:
placing a custom fit device within a user's oral cavity, the device having an angled front wall and an angled rear wall, each wall with an inner and outer surface, wherein the angles of the front wall and the rear wall form an apex with moldable thermoplastic resin material disposed along the inner surfaces of the front and rear wall, the apex configured to receive the incisal edges of the user's upper incisors; and
positioning the device such that the front wall of the device is adjacent to the labial surface of the user's upper incisors and the inner surface of the rear wall is disposed adjacent to the lingual surface of the upper incisors and the device does not contact the user's lower teeth when the user is in the physiologic rest position; and
placing the device to prevent contact of the user's upper and lower premolars and molars when the user's mandible is closed past the physiologic rest position.

14. The method according to claim 13, further comprising the step of molding the moldable thermoplastic resin material.

15. The method according to claim 13, further comprising the step of heating the moldable thermoplastic resin material to a molding temperature of approximately 150 degrees Fahrenheit.

16. The method according to claim 13, wherein the combined thickness of the device's rear wall and the moldable thermoplastic resin material prior to custom molding is approximately 1.75 millimeters.

17. The method according to claim 13, wherein the device preventing contact between the user's posterior teeth comprises the device contacting at least one of the user's lower incisors at an area of contact only within the user's freeway space.

18. The method according to claim 17, wherein contact on the device by at least one of the user's lower incisors proprioceptively directs the user's mandible to the physiologic rest position.

19. A method for manufacturing an oral device to be custom fit for a user, the method comprising:
forming a shell having an angled front wall and an angled rear wall, each wall with an inner and outer surface, wherein the angles of the front wall and the rear wall are configured to receive the incisal edges of the user's upper incisors;
configuring the inner surface of the front wall of the device to fit against the labial surface of the user's upper incisors;
configuring the inner surface of the rear wall to fit against the lingual surface of the user's upper incisors within the user's freeway space;
configuring the device not to contact the user's lower teeth when the user's mandible is in the physiologic rest position; and
adhering to the inner surfaces of the front and rear walls a moldable thermoplastic resin material.

20. The method of claim 19, wherein the shell is formed from plastic.

21. The method of claim 19, wherein the moldable thermoplastic resin material is capable of being molded at a temperature of approximately 150 degrees Fahrenheit.

22. The method of claim 19, further comprising configuring the inner surface of the front wall to fit substantially flush against the labial surface of the user's upper incisors and the inner surface of the real wall to fit substantially flush against the lingual surface of the user's upper incisors.

23. An intra-oral device custom fit for a user, comprising:
a body having a substantially angled front wall and a substantially angled rear wall, the front wall having an inner and outer surface and the rear wall having an inner and outer surface;
moldable thermoplastic resin material disposed along the inner surface of the front and rear walls;
wherein the front and rear walls are configured to receive the incisal edges of the user's upper incisors;
wherein the device is configured not to contact the user's lower teeth when the user is in the physiologic rest position;
wherein the outer surface of the rear wall is configured to fit within the user's freeway space and to prevent contact of the user's upper and lower premolars and molars when the user's mandible closes past the physiologic rest position;
and
wherein the moldable thermoplastic resin material is capable of being molded by the user.

24. The device of claim 23,
wherein the inner surface of the front wall is configured to be placed adjacent to the labial surface of the user's upper incisors; and
wherein the inner surface of the rear wall is configured to be placed adjacent to the lingual surface of the user's upper incisors.

25. The device of claim 23,
wherein the device is configured to contact at least one lower incisor at an area of contact only within the user's freeway space.

26. An intra-oral device custom fit for a user, comprising:
a body having a substantially angled front wall and a substantially angled rear wall, the front wall having an inner and outer surface and the rear wall having an inner and outer surface;
wherein the front and the rear walls of the device are configured to receive the incisal edges of a user's upper incisors;
wherein the rear wall is configured to fit within the user's freeway space and against the rear of the user's upper incisors to permit the incisal edge of the user's lower incisors to be located higher than the incisal edge of the user's upper incisors without the user's lower incisors contacting the device; and
wherein the device is configured to prevent contact of the user's upper and lower premolars and molars when the user's mandible closes past the physiologic rest position.

27. The device of claim 26, wherein the rear wall is configured to fit substantially flush against the rear of the user's upper incisors.

* * * * *